_(12)_ United States Patent
Ravenscroft et al.

(10) Patent No.: US 6,258,026 B1
(45) Date of Patent: *Jul. 10, 2001

(54) REMOVABLE EMBOLUS BLOOD CLOT FILTER AND FILTER DELIVERY UNIT

(75) Inventors: Adrian C. Ravenscroft, Milton; Stephen J. Kleshinski, Scituate, both of MA (US)

(73) Assignee: Nitinol Medical Technologies, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/360,654

(22) Filed: Jul. 26, 1999

Related U.S. Application Data

(63) Continuation-in-part of application No. 09/160,384, filed on Sep. 25, 1998, now Pat. No. 6,007,558.

(51) Int. Cl.$^7$ ................................................ A61M 29/00

(52) U.S. Cl. .......................................... 600/200; 608/198

(58) Field of Search ................................. 606/200, 198, 606/194, 191, 127, 113

(56) References Cited

U.S. PATENT DOCUMENTS

| 4,425,908 | 1/1984 | Simon | 128/1 |
|---|---|---|---|
| 4,817,600 | * 4/1989 | Herms et al. | 606/200 |
| 5,108,418 | 4/1992 | Lefebvre | 606/200 |
| 5,133,733 | 7/1992 | Rasmussen et al. | 606/200 |
| 5,242,462 | 9/1993 | El-Nounou et al. | 606/200 |
| 5,370,657 | 12/1994 | Irie | 606/200 |
| 5,601,595 | * 2/1997 | Smith | 606/200 |
| 5,800,457 | 9/1998 | Gelbfish | 606/200 |
| 5,853,420 | 12/1998 | Chevillon et al. | 606/200 |

OTHER PUBLICATIONS

Morris Simon and Aubrey M. Palestrant "Transvenous Devices for the Management of Pulmonary Embolism", Cardiovascular and Interventional Radiology by Springer–Verlag 1980, 308–318, 1980.

Morris Simon, M.D., Roy Kaplow, Ph.D, Edwin Salzman, M.D., and David Freiman, M.D., A Vena Cava Filter Using Thermal Shape Memory Alloy, Radiology, vol. 125, No. 1 pp. 89–94.

James Hansen, "Metals that Remember", Science 81, Jun., pp. 44–47.

Morris Simon et al., "Cook "Bird S Nest" Vena Cava Filter", Cook Incorporated, Nov. 1982.

* cited by examiner

Primary Examiner—Henry J. Recla
Assistant Examiner—Lien Ngo
(74) Attorney, Agent, or Firm—Nixon Peabody LLP; Daniel W. Sixbey

(57) ABSTRACT

A blood clot filter which is collapsible toward a central longitudinal axis into a collapsed configuration for insertion into a blood vessel and which is radially expandable outwardly from the longitudinal axis to an expanded configuration for contact with the inner wall of the blood vessel at two longitudinal spaced locations. A first plurality of spaced, elongate arms, in the expanded configuration of the filter, curve outwardly away from the longitudinal axis toward the leading end of the filter to form a first filter basket and to center a hub at the trailing end of the filter within the vessel. A second plurality of spaced elongate legs angle outwardly away from the longitudinal axis toward the leading edge of the filter in the expanded configuration thereof to form a second filter basket opening toward the leading end. To prevent longitudinal movement of the filter, the ends of these legs include hooks, at least a portion of which is of a reduced cross sectional area relative to the cross sectional area of the adjacent leg to permit the hooks to bend and straighten in response to withdrawal force.

15 Claims, 3 Drawing Sheets

REMOVABLE EMBOLUS BLOOD CLOT FILTER AND FILTER DELIVERY UNIT

This application is a continuation-in-part application of U.S. Ser. No. 09/160,384 filed Sep. 25, 1998, now U.S. Pat. No. 6,007,558.

BACKGROUND OF THE INVENTION

In recent years, a number of medical devices have been designed which are adapted for compression into a small size to facilitate introduction into a vascular passageway and which are subsequently expandable into contact with the walls of the passageway. These devices, among others, include blood clot filters which expand and are held in position by engagement with the inner wall of a vein. It has been found to be advantageous to form such devices of a shape memory material having a first, relatively pliable low temperature condition and a second, relatively rigid high-temperature condition. By forming such devices of temperature responsive material, the device in a flexible and reduced stress state may be compressed and fit within the bore of a delivery catheter when exposed to a temperature below a predetermined transition temperature, but at temperatures at or above the transition temperature, the device expands and becomes relatively rigid.

Known self expanding medical devices have been formed of Nitinol, an alloy of titanium and nickel which provides the device with a thermal memory. The unique characteristic of this alloy is its thermally triggered shape memory, which allows a device constructed of the alloy to be cooled below a temperature transformation level to a martensitic state and thereby softened for loading into a catheter in a relatively compressed and elongated state, and to regain the memorized shape in an austenitic state when warmed to a selected temperature above the temperature transformation level, such as human body temperature. The two interchangeable shapes are possible because of the two distinct microcrystalline structures that are interchangeable with a small variation in temperature. The temperature at which the device assumes its first configuration may be varied within wide limits by changing the composition of the alloy. Thus, while for human use the alloy may be focused on a transition temperature range close to 98.6° F., the alloy readily may be modified for use in animals with different body temperatures.

U.S. Pat. No. 4,425,908 to Simon discloses a very effective blood clot filter formed of thermal shape memory material. This filter, like most previously developed vena cava filters such as those also shown by U.S. Pat. Nos. 5,108,418 to Lefebvre, 5,133,733 to Rasmussen et al., 5,242,462 to El-Nounou et al., 5,800,457 to Gelbfish and 5,853,420 to Chevillon et al. is a permanent filter which, when once implanted, is designed to remain in place. Such filters include structure to anchor the filter in place within the vena cava, such as elongate diverging legs with hooked ends that penetrate the vessel wall and positively prevent migration in either direction longitudinally of the vessel. The hooks on filters of this type are rigid and will not bend, and within two to six weeks after a filter of this type has been implanted, the endothelium layer grows over the diverging legs and positively locks the hooks in place. Now any attempt to remove the filter results in a risk of injury to or rupture of the vena cava.

A number of medical procedures subject the patient to a short term risk of pulmonary embolism which can be alleviated by a filter implant. In such cases, patients are often adverse to receiving a permanent implant, for the risk of pulmonary embolism may disappear after a period of several weeks or months. However, most existing filters are not easily or safely removable after they have remained in place for more than two weeks, and consequently longer term temporary filters which do not result in the likelihood of injury to the vessel wall upon removal are not available.

In an attempt to provide a removable filter, two filter baskets have been formed along a central shaft which are conical in configuration, with each basket being formed by spaced struts radiating outwardly from a central hub for the basket. The central hubs are held apart by a compression unit, and the arms of the two baskets overlap so that the baskets face one another. Devices of this type require the use of two removal devices inserted at each end of the filter to draw the baskets apart and fracture the compression unit. The end sections of the arms are formed to lie in substantially parallel relationship to the vessel wall and the tips are inclined inwardly to preclude vessel wall penetration. If a device of this type is withdrawn before the endothelium layer grows over the arms, vessel wall damage is minimized. However, after growth of the endothelium layer the combined inward and longitudinal movement of the filter sections as they are drawn apart can tear this layer. U.S. Pat. No. 5,370,657 to Irie is illustrative of a prior art removable filter of this type which requires two removal devices.

SUMMARY OF THE INVENTION

It is a primary object of the present invention to provide a vessel implantable filter of shape memory material having temperature induced austenitic and martensite states which maybe easily removed by a single removal device after an extended period of time without significantly injuring the vessel wall.

Another object of the present invention is to provide a blood clot filter of shape memory material which operates in a temperature induced austenitic state to exert a force on the wall of a vessel by means of oppositely disposed legs to maintain the filter in place, but which may easily be removed after the endothelium layer has covered the ends of the filter legs without significant damage to the vessel wall.

A further object of the present invention is to provide a novel and improved vessel implantable filter having a group of arms and a group of legs which incline from a central axis. The ends of the arms in the group of arms are oriented to engage a vessel wall to orient and center the filter in the vessel, and the ends of the legs of the group of legs are oriented to engage the vessel wall to prevent longitudinal movement of the filter along the vessel. The ends of at least some of the legs are provided with hooks configured to be more elastic than the legs to permit the hooks to straighten in response to a withdrawal force to facilitate withdrawal from the endothelium layer without risk of significant injury to the vessel wall. In some cases, similar hooks can be formed on the ends of at least some of the arms.

Yet another object of the present invention is to provide a novel and improved vessel implantable filter having one or more expandable appendages which engage the wall of the vessel. An elastic hook is formed on the free end of an appendage to pierce the vessel wall and insure that the filter does not migrate in response to normal respiratory functions or in the event of a massive pulmonary embolism. The hook is formed to have a maximum migration force, and when subjected to forces below the maximum migration force, the hook retains its shape. When subjected to forces above the maximum migration force, the hook straightens and can be withdrawn without significant damage to the vessel wall.

A further object of the present invention is to provide a novel and improved vessel implantable filter having a plurality of expandable appendages which engage the wall of a vessel. Three to twelve of such appendages are provided which have an elastic hook formed on the free end of the appendage to pierce the vessel wall and insure that the filter does not migrate when subjected to a pressure gradient falling within a range of from 10 mmHg to 120 mmHg in a 28 mm vessel (filter migration resistance). Each hook is formed to have a maximum migration force, and when subjected to forces below the maximum migration force, the hook retains its shape. When subjected to forces above the maximum migration force, the hook straightens and can be withdrawn without significant damage to the vessel wall. The maximum migration force for each hook is dependent upon the desired total filter migration resistance and the number of hooks formed on the filter.

A still further object of the present invention is to provide a novel and improved removable embolus blood clot filter and filter delivery unit designed to insure delivery of the filter in a centered orientation to a precise location within a vessel. The filter delivery unit includes an elongate pusher wire of shape memory material having temperature induced austenitic and martensite states, with a handle at one end and a filter engaging spline at the opposite end. Spaced inwardly from the spline is a pusher pad which is longitudinally slotted to receive the elongate appendages of the filter. The pusher wire is reduced in diameter between the spline and pusher pad at a point adjacent to the pusher pad to impart a directional hinge to the pusher wire at the reduced portion.

According to the invention, a resilient blood clot filter is inwardly radially collapsible toward its longitudinal axis into a collapsed configuration for insertion into a body vessel, but is adapted for automatic radial expansion into contact with the inner wall of the vessel at two longitudinally spaced peripheral locations therein. The filter has leading and trailing ends and comprises a plurality of wires. The wires, in the normal expanded configuration of the filter, are in the form of a plurality of elongated arms and legs with openings between the wires to provide filter baskets opening at the leading end of the filter. The wires have peripheral portions for contact with the inner wall of the vein at two longitudinally spaced peripheral locations. The arms operate to center the filter while the legs terminate in hooks which anchor the filter but which straighten in response to force applied at the trailing end of the filter to facilitate removal of the filter.

To provide a filter that is inwardly radially collapsible from its normally expanded configuration toward its longitudinal axis into a collapsed configuration for insertion into a body vessel, the blood clot filter is preferably formed from a plurality of wire portions composed of a thermal shape memory material having a first, low-temperature condition and a second, high-temperature condition. The material in its low-temperature condition is relatively pliable (so that the wire portions may be straightened) and in its high-temperature condition is resiliently deformable and relatively rigid, and takes a predetermined functional form.

In the high-temperature condition of the material, the filter comprises coaxial first and second filter baskets, each filter basket being generally symmetrical about the longitudinal axis of the filter with both filter baskets being concave relative to the filter leading end.

DETAILED DESCRIPTION

By forming the body of a blood clot filter of a Nitinol alloy material, such as Nitinol wire, transition between the martensitic and austenitic states of the material can be achieved by temperature transitions above and below a transition temperature or transition temperature range which is at or below body temperature. Such controlled temperature transitions have conventionally been employed to soften and contract the Nitinol filter body to facilitate insertion into a catheter and to subsequently expand and rigidify the body within a vascular or other passageway. Although the filters of the present invention are preferably formed from a temperature responsive shape memory material, such as Nitinol, they can also be formed of a compressible spring metal such as stainless steel or a suitable plastic.

Figure 1:
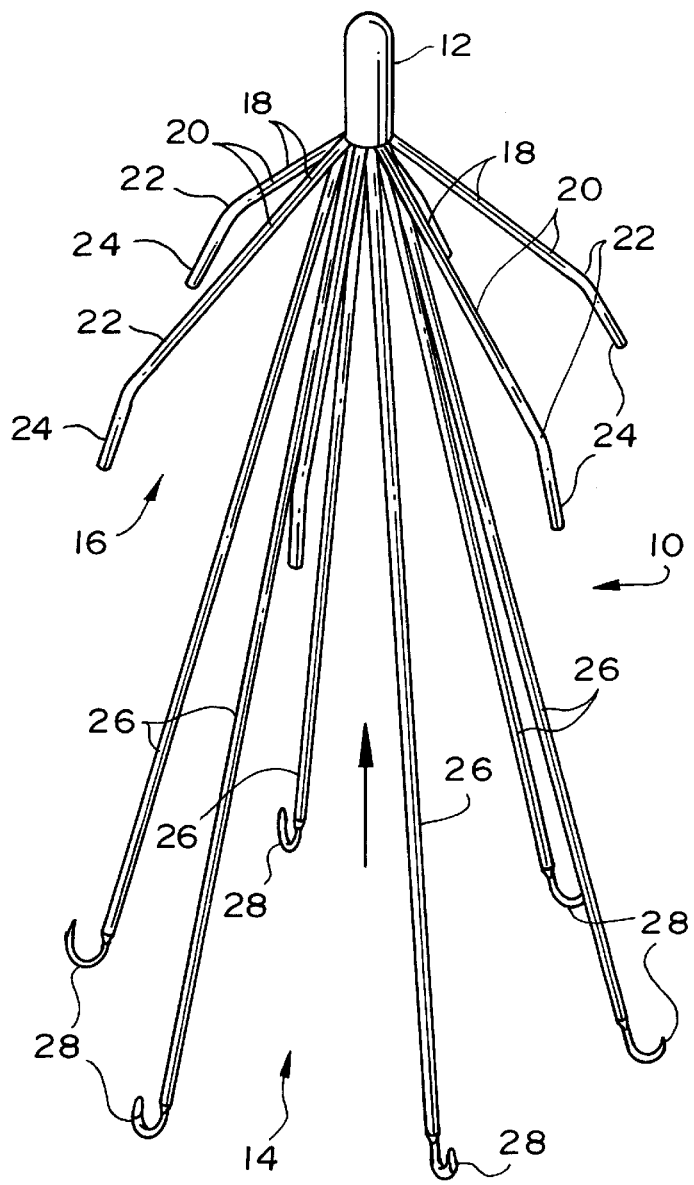
FIG. 1 is a view in side elevation of an expanded blood clot filter of the present invention.

Referring now to FIG. 1, an expanded blood clot filter 10 is illustrated which is made from sets of elongate metal wires. The wires are held together at the filter trailing end by a hub 12 where they are plasma welded together and to the hub or otherwise joined. In the low temperature martensite phase of wires made of thermal shape memory material, the sets of wires can be straightened and held in a straight form that can pass through a length of fine plastic tubing with an internal diameter of approximately 2 mm (#8 French catheter). In its high temperature austenitic form, the filter 10 recovers a preformed filtering shape as illustrated by FIG. 1. Similarly, wires of spring metal can be straightened and compressed within a catheter or tube and will diverge into the filter shape of FIG. 1 when the tube is removed.

In its normal expanded configuration or preformed filtering shape, filter 10 is a double filter, having a first forwardly disposed filter basket section 14 at the forward or leading end of the filter and a second forwardly disposed filter basket section 16. The two filter basket sections provide peripheral portions which can both engage the inner wall of a body vessel 17 at two longitudinally spaced locations, and the two filter basket sections are generally symmetrical about a longitudinal axis passing through the hub 12. On the other hand, the second forwardly disposed filter basket section 16, which is primarily a centering unit, may not always touch the vessel wall on all sides.

The second filter basket section 16 is formed from short lengths of wire which form arms 18 that extend angularly, outwardly and then downwardly from the hub 12 toward the forward end of the filter 10. Each arm 18 has a first arm section 20 which extends angularly outwardly from the hub 12 to a shoulder 22, and an outer arm section 24 extends angularly from the shoulder toward the forward end of the filter. The outer arm sections 24 are substantially straight lengths with ends which lie on a circle at their maximum divergence and engage the wall of a vessel at a slight angle (preferably within a range of from ten to forty-five degrees) to center the hub 12 within the vessel. For a filter which is to be removed by grasping the hub 12, it is important for the hub to be centered. Normally, there are six wires 18 of equal length extending radially outward from the hub 12 and circumferentially spaced, such as for example by sixty degrees of arc.

Figure 4:
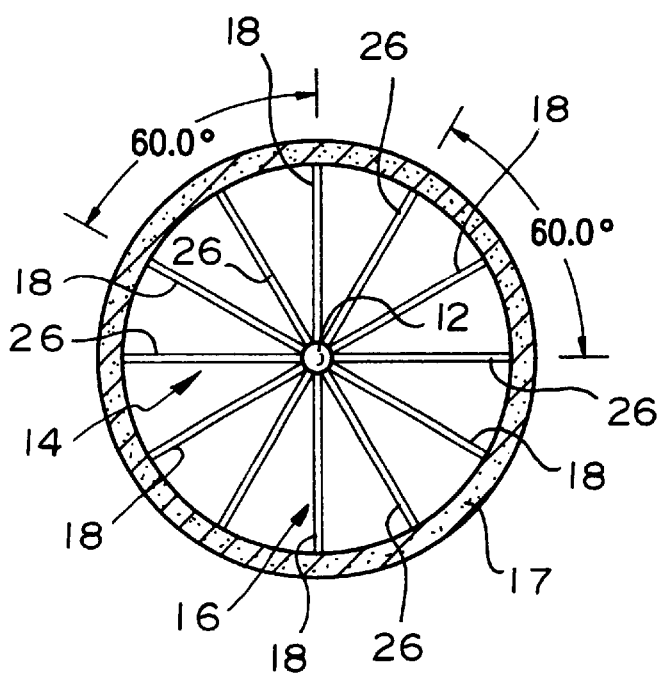
FIG. 4 is a cross sectional view of the blood clot filter of the present invention in place in a blood vessel.
Figure 7:
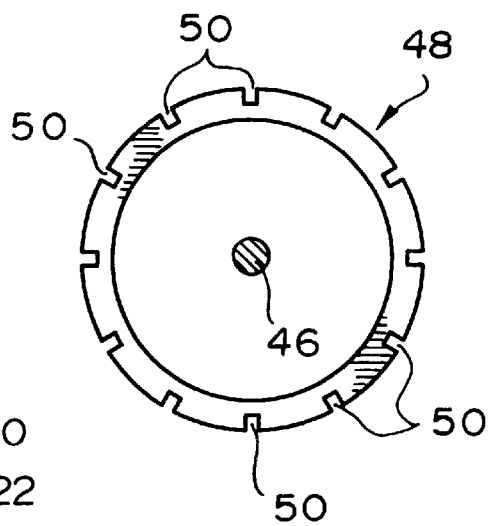
FIG. 7 is an enlarged view in end elevation of the pusher pad for the filter delivery unit of FIG. 6.

The first filter basket section 14 is the primary filter and can include up to twelve circumferentially spaced straight wires 26 forming downwardly extending legs which tilt outwardly of the longitudinal axis of the filter 10 from the hub 12. Six of the wires 26 are shown in FIG. 1, and may be of equal length, but normally they are not so that hooks 28 at the ends of the wires will fit within a catheter without becoming interconnected. The wires 26 are preferably much longer than the wires 18, and have tip sections which are uniquely formed, outwardly oriented hooks 28 which lie on a circle at the maximum divergence of the wires 26. There may be from three to twelve of the wires 26 formed with hooks 28, although in some instances, the wire arms 18 may include similarly formed hooks at the free ends thereof. The wires 26, in their expanded configuration of FIG. 1, are at a slight angle to the vessel wall, preferably within a range of from ten to forty-five degrees, while the hooks 28 penetrate the vessel wall to anchor the filter against movement. The wires 26 are radially offset relative to the wires 18 and may be positioned halfway between the wires 18 and also may be circumferentially spaced by sixty degrees of arc as shown in FIG. 4. Thus the combined filter basket sections 14 and 16 can provide a wire positioned at every thirty degrees of arc at the maximum divergence of the filter sections. With reference to the direction of blood flow shown by the arrow in FIG. 1, the filter section 14 forms a concave filter basket opening toward the leading end of the filter 10 while the filter section 16 forms a concave filter basket opening toward the leading end of the filter 10 downstream of the filter section 14.

The structure of the hooks 28 is important. As in the case of hooks formed on the legs of previously known permanent vena cava filters, these hooks 28 penetrate the vessel wall when the filter 10 is expanded to anchor the filter in place and prevent filter migration longitudinally of the vessel in either direction. However, when these hooks are implanted and subsequently covered by the endothelium layer, they and the filter can be withdrawn without risk of significant injury or rupture to the vena cava. Minor injury to the vessel wall due to hook withdrawal such as damage to the endothelial layer or local vena cava wall puncture is acceptable. However, previous filters with rigid anchoring hooks could not be withdrawn without causing unacceptable vessel tearing or local hemorrhage.

Figure 2:
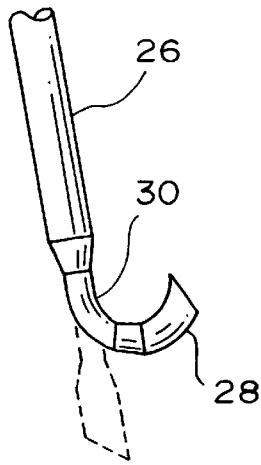
FIG. 2 is a view in side elevation of a hook for a leg of the filter of FIG. 1.

With reference to FIGS. 1 and 2, each hook 28 is provided with a juncture section 30 between the curvature of the hook and the leg 26 (or arm 18) to which the hook is attached. This juncture section is considerably reduced in cross section relative to the cross section of the leg 26 (or arm 18) and the remainder of the hook. The juncture section is sized such that it is of sufficient stiffness when the legs 26 (or arms 18) are expanded to permit the hook 28 to penetrate the vena cava wall. However, when the hook is to be withdrawn from the vessel wall, withdrawal force to which the hook is subjected will cause flexure in the juncture section 30 so that the hook moves toward a position parallel with the axis of the leg 26 (or arm 18) as shown in broken lines in FIG. 2. With the hook so straightened, it can be withdrawn without tearing the vessel wall leaving only a small puncture.

Figure 3:
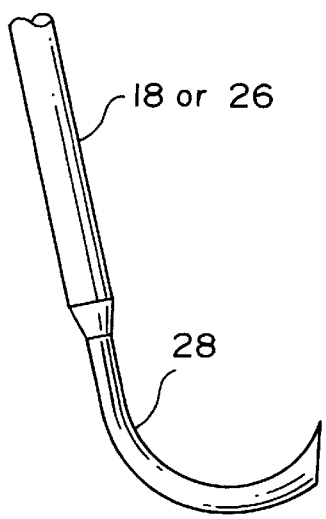
FIG. 3 is a view in side elevation of a second embodiment of a hook for a leg of the filter of FIG. 1.

With reference to FIG. 3, it will be noted that the entire hook 28 can be formed with a cross section throughout its length which is less than that of the leg 26 (or arm 18). This results in straightening of the hook over its entire length in response to a withdrawal force. This elasticity in the hook structure prevents the hook from tearing the vessel wall during withdrawal.

As previously indicated, while it is possible that the filter could be made from ductile metal alloys such as stainless steel, titanium, or elgiloy, it is preferable to make it from nitinol. Nitinol is a low modulus material which allows the arms and legs of the device to be designed to have low contact forces and pressures while still achieving sufficient anchoring strength to resist migration of the device. The force required to cause opening of the hooks 28 can be modulated to the total force required to resist filter migration. This is accomplished by changing the cross sectional area or geometry of the hooks, or by material selection.

In addition to temperature sensitivity, nitinol, when in the temperature induced austenitic state, is also subject to stress sensitivity which can cause the material to undergo a phase transformation from the austenitic to the martensitic state while the temperature of the material remains above the transition temperature level. By reducing a portion or all of the cross sectional area of the hooks 28 relative to that of the legs 26 (or arms 18), stress is concentrated in the areas of reduced cross section when longitudinal force is applied to the hub 12 in the direction of the trailing end of the filter to remove the filter, and the hooks become elastic and straighten. Thus the hooks, whether formed of nitinol, spring metal or plastic, are designed to bend toward a more straight configuration when a specific hook migration force is applied and spring back to their original shape once the hook migration force has been removed. The force or stress which is required to deform the hook can be correlated to the force applied to each hook of the device when it is fully occluded and the blood pressure in the vessel is allowed to reach 50 mmHg. This force is approximately 70 gms on each leg of a six leg device for 50 mmHg. pressure differential in a 28 mm vessel. The desired total migration resistance force for the filter is desireably 420 gms, and more legs 26 with hooks 28 can be added to lower maximum migration force for each hook. The load on the filter would be correspondingly smaller in vessels of smaller diameter. The object is to have the hook perform as an anchoring mechanism at a predetermined filter migration resistance force within a range of 10 mmHg up to 120 mmHg. Having maintained its geometry at a predetermined filter migration resistance force within this range, the hook should begin to deform in response to a higher force applied in the direction of the filter trailing end and release at a force substantially less than that which would cause damage to the vessel tissue. It is the ability of the hook to straighten somewhat that allows for safe removal of the device from the vessel wall.

After the filter 10 has remained in place within a vessel for a period of time in excess of two weeks, the endothelium layer will grow over the hooks 28. However, since these hooks, when subjected to a withdrawal force become substantially straight sections of wire oriented at a small angle to the vessel wall, the filter can be removed leaving only six pin point lesions in the surface of the endothelium. To accomplish this, a catheter or similar tubular unit is inserted over the hub 12 and into engagement with the arms 18. While the hub 12 is held stationary, the catheter is moved downwardly forcing the arms 18 downwardly, and subsequently the arms 26 are engaged and forced downwardly thereby withdrawing the hooks 28 from the endothelium layer. Then the hub 12 is drawn into the catheter to collapse the entire filter 10 within the catheter. When the filter is formed from shape memory material, cooling fluid can be passed through the catheter to aid in collapsing the filter.

The primary objective of the hooks 28 is to ensure that the filter does not migrate during normal respiratory function or in the event of a massive pulmonary embolism. Normal inferior vena cava (IVC) pressures are between 2–5 mmHg. An occluded IVC can potentially pressurize to 35 mmHg below the occlusion. To ensure filter stability, a 50 mmHg pressure drop across the filter may therefore be chosen as the design criteria for the filter migration resistance force for the removable filter 10. When a removal pressure is applied to the filter that is greater than 50 mmHg, the hooks 28 will deform and release from the vessel wall. The pressure required to deform the hooks an be converted to force by the following calculations.

$$\text{Since } 51.715 \text{ mmHg} = 1.0^{lb}/\text{in}^2$$

$$50 \text{ mmHg} = \frac{50}{51.715} = 0.9668^{lb}/\text{in}^2$$

For a 28 mm vena cava $$A = \frac{\pi}{4} 28^2 \text{ mm}^2 = 615.4 \text{ mm}^2 = 0.9539 \text{ in}^2$$

Migration force is calculated by $$P = \frac{F}{A} \quad F = P \times A$$

$$0.9668^{lb}/\text{in}^2 \times 0.9539 \text{ in}^2 = 0.9223 \text{ lb} = 418.7 g$$

It is important to recognize that as vena cava diameter increases so does the force required to resist 50 mmHg of pressure.

Depending on the number of filter hooks, the strength of each can be calculated. For a device that has six hooks:

$$\text{Hook Strength} = \frac{\text{Filter Migration Resistance Force}}{\text{Number of Hooks}}$$

$$= \frac{418.7}{6} = 69.7 g$$

Each hook must be capable of resisting approximately 70 grams of force for the filter 10 to resist 50 mmHg pressure gradient in a 28 mm vessel.

To prevent excessive vessel trauma the individual hook needs to be relatively weak. By balancing the number hooks and the individual hook strength, minimal vessel injury can be achieved while still maintaining the 50 mmHg pressure gradient criteria, or some other predetermined pressure gradient criteria within a range of from 10 mmHg to 120 mmHg.

Figure 5:
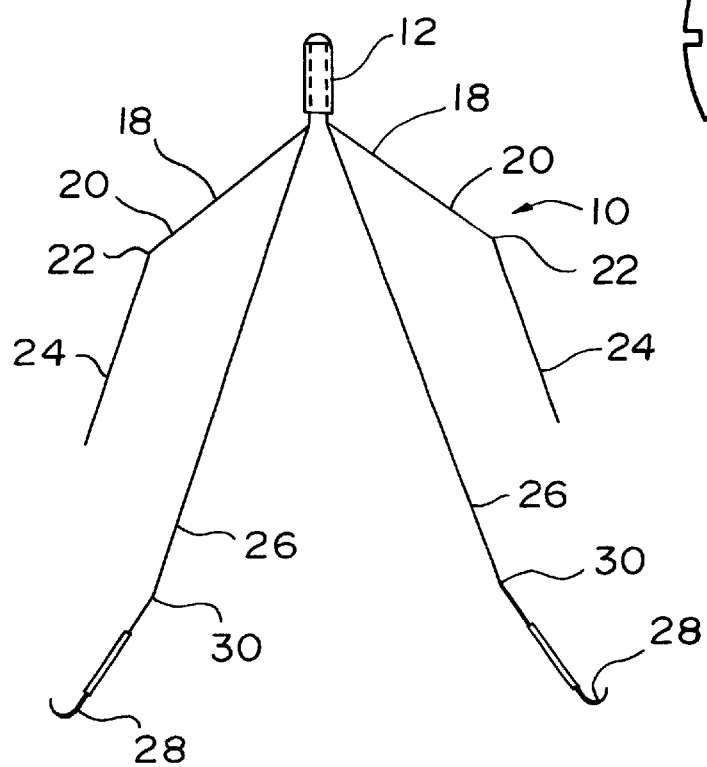
FIG. 5 is a diagrammatic view of a second embodiment of the leg structure for the blood clot filter of the present invention.
Figure 6:
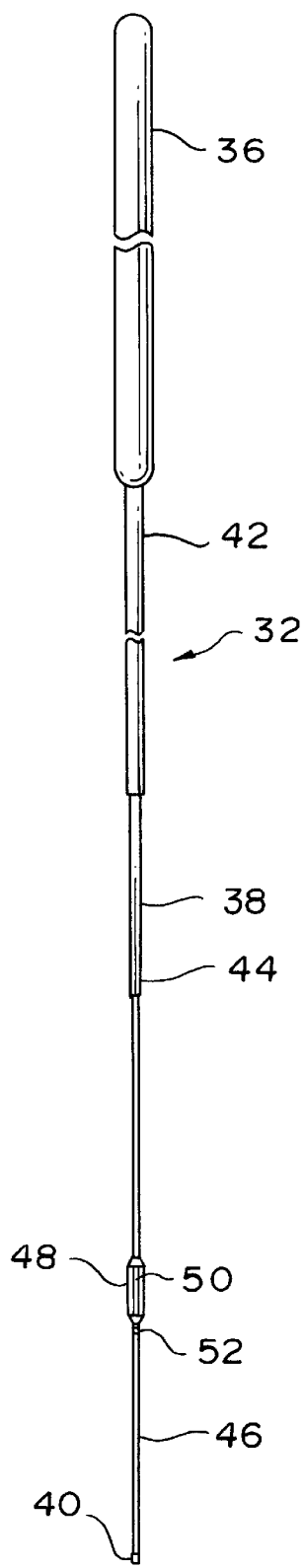
FIG. 6 is a plan view of the filter delivery unit of the present invention.

Referring to FIG. 5, the legs 26 may be angled outwardly from a shoulder 30 adjacent to but spaced from the outer end of each leg. When the legs are released from compression in a catheter or other tube into a body vessel, this bend in each leg insures that the hooks 28 are, in effect, spring loaded in the tube and that they will not cross as they are deployed from the tube. Since the legs angle outwardly from the shoulders 30, the hooks 28 are rapidly deployed outwardly as the insertion tube is withdrawn.

The filter delivery unit 32 is adapted to deliver the filter 10 through a catheter or delivery tube 34 to a precise, centered position within a body vessel. The filter delivery unit includes a handle 36 at one end, and an elongate pusher wire 38 extends outwardly from the handle 36. At the free end of the pusher wire is an enlarged filter engaging pusher pad 40.

The elongate pusher wire 38 is preferably formed of superelastic material and may be formed of thermally responsive shape memory material, such as nitinol. The pusher wire includes sections 42, 44 and 46 which progressively decrease in cross section beginning at the handle 36. The temperature transformation level of the pusher wire is such that when the wire is encased in a catheter or delivery tube, it remains in a martensitic state and is therefore somewhat pliable and flexible so that it can conform to curvatures in a catheter or delivery tube which passes through a body vessel. As the delivery tube is withdrawn, body temperature causes the exposed portions of the pusher wire to assume the move rigid austenitic state for filter positioning.

Figure 8:
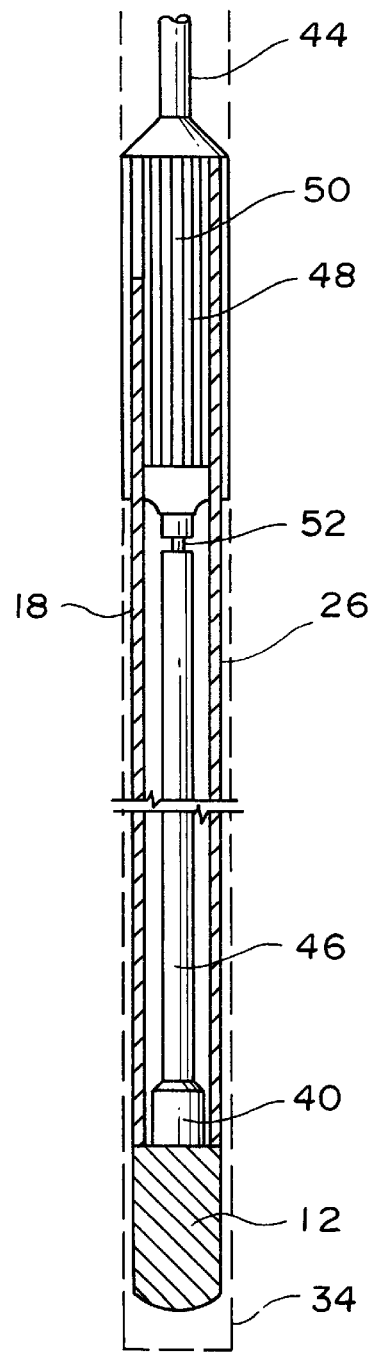
FIG. 8 is an enlarged view of the end section of the filter delivery unit of FIG. 6 in engagement with a filter.

A slotted spline 48 is secured to the pusher wire 38 between the sections 44 and 46. The pusher pad is provided with a plurality of spaced, peripherally arranged, longitudinally extending grooves 50 of sufficient number to individually receive the legs 26 of a filter 10. The spline is spaced from the pusher pad 40 for a distance less than the length of the filter legs 26 so that the legs can be received in the grooves 50 when the pusher pad engages the filter hub 12 as shown in FIG. 8. It will be noted that the pusher wire section 46 is reduced in cross section at 52 adjacent to the spline 48.

To load the filter delivery unit 32 to insert a filter 10 into a body vessel, the pusher wire section 46 is inserted from the leading end of the filter 10 under the arms 18 and legs 26 until the pusher pad 40 engages the underside of the hub 12 at the apex of the filter as shown in FIG. 8. Then the legs 26 of the filter, two being shown for purposes of illustration in FIG. 8, are inserted into the grooves 50 in the spline, and the arms 18 are spirally wrapped around the spline. The pusher wire, with the filter in place, is inserted into a catheter or delivery tube 34. When the catheter or delivery tube with the filter 10 is at a desired location within a body vessel, it is removed from around the delivery unit and filter to expose the filter. First the hub 12 of the filter is exposed and then the pusher wire section 46 emerges. When the pusher wire is formed of thermal shape memory material, the emergence of wire section 46 causes this section, with the exception of the portion of reduced cross section 52, to transform to the austenitic state and to become more rigid. As the filter pad 48 emerges, the centering arms 18 of the filter 10 are exposed and released and transform to the austenitic state to achieve radial expansion outwardly toward the vessel wall. If the filter is not centered in the vessel, some of the arms 18 will engage the vessel wall and apply stress to the reduced cross section portion 52 of the pusher wire section 46. Stress causes this portion 52 to remain in the flexible martensitic state, and the pusher wire section 46 will pivot at the portion 52 to permit radial movement of the spline 40 in all directions to aid the arms 18 in centering the filter 10 within the vessel. Thus the portion 52 provides a directional hinge for centering the filter.

With the filter centered, the legs 26 are exposed and expand radially to engage the vessel wall and anchor the filter against migration. The pusher wire and catheter or delivery tube are now withdrawn from the body vessel.

When the pusher wire is formed of flexible material which is not a thermal, shape memory material, the reduced cross sectional portion 52 to the pusher wire section 46 has greater flexibility than the remainder of the pusher wire and thus forms a flexible, directional hinge to aid in centering the filter in the manner previously described.

What is claimed is:

1. A removable blood clot filter having leading and trailing ends and a filter central longitudinal axis and which is collapsible in a collapsed configuration toward said filter longitudinal axis for insertion into a blood vessel and is radially expandable outwardly from said filter longitudinal axis to an expanded configuration to contact and penetrate an inner wall of said blood vessel to provide a filter migration resistance force sufficient to prevent filter migration in response to blood pressure within said blood vessel comprising:

a plurality of elongate, spaced appendages having first and second ends, the first ends of said plurality of elongate spaced appendages being formed to extend outwardly toward said filter leading end away from said filter longitudinal axis in the expanded configuration of said filter, each of a plurality of said elongate spaced appendages having an appendage longitudinal axis and a pointed hook formed at the second end thereof which extends laterally outward relative to said appendage longitudinal axis in a direction away from said filter longitudinal axis to engage and penetrate the vessel inner wall in the expanded configuration of said filter, each said hook being formed with a maximum migration force such that a force above said maximum migration force applied to said hook as a result of a withdrawal force in excess of said filter migration resistance force applied to the trailing end of said filter in a direction away from the filter leading end will cause said hook to straighten and bend toward the filter longitudinal axis and toward a configuration parallel with the appendage longitudinal axis, to facilitate removal of the hook from the vessel wall without tearing the vessel wall, the sum of the maximum migration forces for the hooks for said filter being substantially equal to the filter migration resistance force.

2. The removable blood clot filter of claim 1 wherein each said hook curves laterally relative to said appendage longitudinal axis and outwardly away from said filter longitudinal axis to a pointed end.

3. The removable blood clot filter of claim 2 wherein at least a portion of said hook is formed with a cross sectional area of reduced size relative to the cross sectional area of said appendage to provide the maximum migration force above which the hook will bend toward a straightened configuration.

4. The removable blood clot filter of claim 1 wherein said hooks are formed to impart a filter migration resistance force to said filter within a range of from 10 mmHg to 120 mmHg.

5. The removable blood clot filter of claim 1 wherein said elongate appendages include a plurality of spaced elongate substantially straight legs and a plurality of spaced, elongate arms, both said elongate legs and arms having first ends mounted adjacent to said longitudinal axis, said arms in the expanded configuration of said filter each extending in a substantially straight line angularly outward away from the longitudinal axis to an elbow spaced between said first and second ends of said arm and then angularly away from said elbow in a substantially straight line to the second end of said arm.

6. The removable blood clot filter of claim 5 wherein said elongate legs extend toward the leading end of said filter to form a first filter basket and each said elongate arm angles outwardly from the longitudinal axis of said filter toward the leading end of said filter and then angles away from said elbow toward the leading end of said filter to form a second filter basket.

7. The removable blood clot filter of claim 4 wherein said hooks are formed to impart a filter migration resistance force to said filter of substantially 50 mmHg.

8. The removable blood clot filter of claim 5 wherein said hooks are formed to impart a filter migration resistance force to said filter within a range of from 10 mmHg to 120 mmHg.

9. The removable blood clot filter of claim 5 wherein said hook curves laterally relative to said appendage longitudinal axis and outwardly from said filter longitudinal axis to a pointed end.

10. The removable blood clot filter of claim 9 wherein at least a portion of said hook is formed with a cross sectional area of reduced size relative to the cross sectional area of said appendage to provide the maximum migration force above which the hook will bend toward a straightened configuration.

11. The removable blood clot filter of claim 3 wherein the entire cross sectional area along the length of each said hook is of reduced size relative to the cross sectional area of the appendage bearing said hook.

12. The removable blood clot filter of claim 3 wherein said elongate appendages and hooks are formed of thermal shape memory material having a temperature transformation level below which said material is relatively pliable and compressible and above which said material is self-expandable to a substantially rigid, predetermined configuration, and wherein withdrawal force applied to the trailing end of said filter results in stress being concentrated in the reduced cross sectional area of said hooks.

13. The removable blood clot filter of claim 10 wherein the entire cross sectional area along the length of said hook is of reduced size relative to the cross sectional area of the appendage bearing the hook.

14. The removable blood clot filter of claim 10 wherein each said hook is formed integrally with the second end of an elongate leg, said hook being formed with a joinder section adjacent to said elongate leg, said joinder section having a cross sectional area which is reduced in size relative to the cross sectional area of said elongate leg.

15. The removable blood clot filter of claim 10 wherein said elongate, legs and hooks are formed of thermal shape memory material having a temperature transformation level below which said material is relatively pliable and compressible and above which said material is self-expandable to a substantially rigid, predetermined configuration, and wherein withdrawal force applied to the trailing end of said filter results in stress being concentrated in the reduced cross sectional area of said hooks.

* * * * *